US012780964B2

(12) United States Patent
Sakano et al.

(10) Patent No.: US 12,780,964 B2
(45) Date of Patent: Nov. 3, 2026

(54) COMPOSITION

(71) Applicant: Kuraray Co., Ltd., Okayama (JP)

(72) Inventors: Takeshi Sakano, Hiroshima-ken (JP); Makoto Okamoto, Okayama-ken (JP)

(73) Assignee: Kuraray Co., Ltd., Okayama (JP)

( * ) Notice: Subject to any disclaimer, the term of this patent is extended or adjusted under 35 U.S.C. 154(b) by 31 days.

(21) Appl. No.: 19/115,200

(22) PCT Filed: Oct. 13, 2023

(86) PCT No.: PCT/JP2023/037277

§ 371 (c)(1),
(2) Date: Mar. 25, 2025

(87) PCT Pub. No.: WO2024/080374

PCT Pub. Date: Apr. 18, 2024

(65) Prior Publication Data

US 2026/0103554 A1 Apr. 16, 2026

(30) Foreign Application Priority Data

Oct. 14, 2022 (JP) ................................ 2022-165677

(51) Int. Cl.

| | |
|---|---|
| ***C08F 210/02*** | (2006.01) |
| ***C07C 19/043*** | (2006.01) |
| ***C07C 19/045*** | (2006.01) |
| ***C07C 21/067*** | (2006.01) |
| ***C07C 21/073*** | (2006.01) |
| ***C07C 69/007*** | (2006.01) |

(52) U.S. Cl.

CPC .......... *C08F 210/02* (2013.01); *C07C 19/043* (2013.01); *C07C 19/045* (2013.01); *C07C 21/067* (2013.01); *C07C 21/073* (2013.01); *C07C 69/007* (2013.01)

(58) Field of Classification Search

CPC ..................................................... C08F 210/02

See application file for complete search history.

(56) References Cited

U.S. PATENT DOCUMENTS

| | | | |
|---|---|---|---|
| 4,891,436 A | 1/1990 | Cohen et al. | |
| 5,202,465 A | 4/1993 | Merger et al. | |
| 2015/0210788 A1 | 7/2015 | Okamoto et al. | |
| 2021/0347721 A1 | 11/2021 | Minamoto et al. | |
| 2024/0270886 A1 * | 8/2024 | Aoyama .................. | C08F 2/38 |

FOREIGN PATENT DOCUMENTS

| | | | |
|---|---|---|---|
| EP | 0110245 | A1 | 6/1984 |
| JP | 59-106438 | A | 6/1984 |
| JP | H04-502007 | A | 4/1992 |
| JP | H05-201922 | A | 8/1993 |
| JP | 2014-034647 | A | 2/2014 |
| WO | 2020/022364 | A1 | 1/2020 |

OTHER PUBLICATIONS

International Search Report issued in International Application No. PCT/JP2023/037277, dated Dec. 19, 2023.

Written Opinion of the International Searching Authority issued in International Application No. PCT/JP2023/037277, dated Dec. 19, 2023.

* cited by examiner

*Primary Examiner* — William D Young

(74) *Attorney, Agent, or Firm* — Morgan, Lewis & Bockius LLP

(57) ABSTRACT

Provided is a composition containing an unsaturated compound and an organic halide, wherein a content of the organic halide in terms of halogen element, based on a content of the unsaturated compound, is 1 ppm by mass or more and 10,000 ppm by mass or less.

8 Claims, No Drawings

COMPOSITION

TECHNICAL FIELD

The present invention relates to a composition.

BACKGROUND ART

2-Methylene-1,3-propanediol diacetate (hereinafter, may be also referred to as "MPDAc") is used as a modifying agent (comonomer) and the like (see Patent Document 1) of, for example, an ethylene-vinyl alcohol copolymer (hereinafter, may be also referred to as "EVOH"). An MPDAc-modified EVOH obtained by saponifying a copolymer of ethylene, a vinyl ester, and MPDAc has enhanced molding processibility while favorable barrier properties are maintained, with respect to an unmodified EVOH. Even in a case of use of a compound provided by substituting a part of atoms of MPDAc, similar effects can be obtained. Hereinafter, MPDAc and the compound provided by substituting a part of atoms of MPDAc are taken together referred to also as "MPDAc, etc.".

PRIOR ART DOCUMENTS

Patent Documents

Patent Document 1: Japanese Unexamined Patent Application, Publication No. 2014-34647

SUMMARY OF THE INVENTION

Problems to be Solved by the Invention

MPDAc, etc. is, as described above, a polymerizable compound, and during, storage, a polymerization inhibitor is added thereto in order to inhibit a polymerization reaction and the like. Prior to carrying out polymerization by using MPDAc, etc., eliminating the polymerization inhibitor added is necessary. However, MPDAc, etc. has a high boiling point of 200° C. or more. Thus, in order to eliminate the polymerization inhibitor from MPDAc, etc. at a low temperature, employing equipment for distillation under reduced pressure is required, thereby leading to low production efficiency.

In this regard, the present inventors have found that during storage, an organic halide plays a role such as a polymerization inhibitor on MPDAc, etc., and meanwhile, a favorable polymerization reaction of MPDAc, etc. is caused at a comparatively high temperature in allowing for the polymerization reaction on MPDAc, etc., without eliminating the organic halide. In addition, a composition having a high content of the organic halide may result in corrosion of a metal container during storage.

The present invention was made in view of such circumstances, and an object of the present invention is to provide a composition containing a polymerizable compound, wherein the composition is superior in storage stability and also enables inhibiting corrosion of a metal during storage.

Means for Solving the Problems

The above-described object is achieved by providing any one of the following:

(1) A composition containing: an unsaturated compound represented by the following formula (1); and an organic halide, wherein a content of the organic halide in terms of halogen element, based on a content of the unsaturated compound is 1 ppm by mass or more and 10,000 ppm by mass or less;

(1)

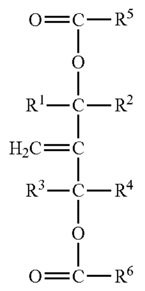

wherein, in the above formula (1), $R^1$, $R^2$, $R^3$, $R^4$, $R^5$, and $R^6$ each independently represent a hydrogen atom or an alkyl group having 1 to 10 carbon atoms.

(2) The composition according to (1), wherein the content of the unsaturated compound is 95% by mass or more;

(3) The composition according to (1) or (2), wherein a content of an inorganic halide in terms of halogen element, based on the content of the unsaturated compound is 10 ppm by mass or less;

(4) The composition according to any one of (1) to (3), wherein the organic halide includes a compound represented by the following formula (2);

(2)

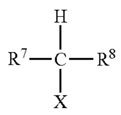

wherein, in the above formula (2): X represents a halogen atom; and $R^7$ and $R^8$ satisfy any one of following requirement A, requirement B, and requirement C, requirement A: $R^7$ represents a group represented by $CR^9R^{10}{=}CR^{11}{-}$ (wherein, $R^9$, $R^{10}$, and $R^{11}$ each independently represent a hydrogen atom, a halogen atom, a monovalent hydrocarbon group, or a monovalent halogenated hydrocarbon group); and $R^8$ represents a hydrogen atom, a halogen atom, a monovalent hydrocarbon group, or a monovalent halogenated hydrocarbon group;

requirement B: $R^7$ represents a secondary or tertiary monovalent hydrocarbon group, or a secondary or tertiary monovalent halogenated hydrocarbon group; and $R^8$ represents a hydrogen atom, a halogen atom, a monovalent hydrocarbon group, or a monovalent halogenated hydrocarbon group;

requirement C: $R^7$ and $R^8$ each independently represent a monovalent hydrocarbon group or a monovalent halogenated hydrocarbon group.

(5) The composition according to (4), wherein $R^7$ and $R^8$ in the above formula (2) satisfy the requirement A;

(6) The composition according to any one of (1) to (5), wherein the organic halide includes a compound having a carbon-carbon unsaturated double bond;

(7) The composition according to any one of (1) to (6), wherein the organic halide includes a compound represented by $C_4H_5X_3$ (wherein, X represents a halogen atom);

(8) The composition according to any one of (1) to (7), which is for use in synthesis of a polymer.

Effects of the Invention

The present invention is capable of providing a composition containing a polymerizable compound, wherein the composition is superior in storage stability and also enables inhibiting corrosion of a metal during storage.

DESCRIPTION OF EMBODIMENTS

The composition of the present invention contains: an unsaturated compound represented by the following formula (1) (hereinafter, may be also referred to as "unsaturated compound (A)"); and an organic halide (hereinafter, may be also referred to as "organic halide (B)"), in which a content of the organic halide (B) in terms of halogen element, based on the content of the unsaturated compound (A) is 1 ppm by mass or more and 10,000 ppm by mass or less.

(1)

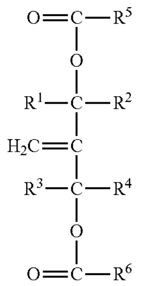

In the above formula (1), $R^1$, $R^2$, $R^3$, $R^4$, $R^5$, and $R^6$ each independently represent a hydrogen atom or an alkyl group having 1 to 10 carbon atoms.

The composition of the present invention is a composition containing a polymerizable compound, wherein the composition is superior in storage stability and also enables inhibiting corrosion of a metal during storage. Although the reason is not certain, the advantage is presumed to result from: the organic halide (B) functioning like a polymerization inhibitor during storage of the unsaturated compound (A); and the organic halide (B), which can be a factor contributing to corrosion of metals, not being excessively present. Moreover, in the composition, a favorable polymerization reaction is caused even in the case of subjecting the composition to the polymerization reaction, without performing a purification operation (an operation for removing the organic halide (B)) such as distillation. This advantage is considered to result from a feature that the organic halide (B) sufficiently exerts the effect of inhibiting the polymerization reaction of the unsaturated compound (A) at temperatures under general storage environments (for example, at a room temperature), whereas the effect of inhibiting the polymerization reaction is hardly exerted at temperatures, for example, 80° C. or higher, for carrying out the polymerization reaction. The reason for this feature is presumed as, for example, in the following: at least a part of the organic halide (B) is present as a highly stable radical at temperatures under general storage environments, thereby being capable of functioning like a polymerization inhibitor by capturing a radical from the unsaturated compound (A) generated due to heat, light, oxygen, and the like, whereas the stability of organic halide (B) radical is relatively lowered at high temperatures.

Hereinafter, each component and the like of the composition of the present invention will be specifically described.

Unsaturated Compound (A)

The unsaturated compound (A) is the compound represented by the above formula (1). In the above formula (1), $R^1$, $R^2$, $R^3$, $R^4$, $R^5$, and $R^6$ each independently represent a hydrogen atom or an alkyl group having 1 to 10 carbon atoms.

Examples of the alkyl group having 1 to 10 carbon atoms which may be represented by each of $R^1$, $R^2$, $R^3$, $R^4$, $R^5$, and $R^6$ in the above formula (1) include a methyl group, an ethyl group, an n-propyl group, an isopropyl group, and the like. The alkyl group having 1 to 10 carbon atoms is preferably an alkyl group having 1 to 3 carbon atoms.

$R^1$, $R^2$, $R^3$, and $R^4$ in the above formula (1) represents preferably a hydrogen atom or an alkyl group having 1 to 3 carbon atoms, and more preferably a hydrogen atom.

$R^5$ and $R^6$ in the above formula (1) each represent preferably a hydrogen atom or an alkyl group having 1 to 3 carbon atoms, more preferably an alkyl group having 1 to 3 carbon atoms, and still more preferably a methyl group.

In a case in which $R^1$, $R^2$, $R^3$, and $R^4$ in the above formula (1) each represent a hydrogen atom, and $R^5$ and $R^6$ each represent a methyl group, the unsaturated compound (A) is 2-methylene-1,3-propanediol diacetate (MPDAc). One type, or two or more types of the unsaturated compound (A) may be used.

A content of the unsaturated compound (A) in the composition of the present invention is not particularly limited and may be, for example, 10% by mass or more, 30% by mass or more, 50% by mass or more, 70% by mass or more, or 90% by mass or more, and is preferably 95% by mass or more, more preferably 99% by mass or more, still more preferably 99.5% by mass or more, and particularly preferably 99.9% by mass or more. In a case in which the unsaturated compound (A) accounts for a large part in the composition of the present invention, the composition can be particularly suitably used as a monomer material. A content of the unsaturated compound (A) in the composition may be 99.9999% by mass or less, or may be 99.999% by mass or less or 99.99% by mass or less.

The unsaturated compound (A) can be produced by a conventionally well-known method. Specifically, the unsaturated compound (A) can be synthesized by: a method of allowing to react 2-methylene-1,3-propanediol with acetic anhydride; a method of allowing to react β-methallyl acetate with acetic acid in the presence of a metal catalyst under an oxygen atmosphere; and the like.

Organic Halide (B)

The organic halide (B) is not particularly limited as long as it is an organic matter containing halogen. Examples of halogen contained in the organic halide (B) include fluorine, chlorine, bromine, iodine, and the like, and chlorine is preferred. In other words, the organic halide (B) is preferably an organic chlorinated product. The organic halide (B) may be constituted from, for example, a carbon atom, a hydrogen atom, and a halogen atom, or may be constituted from a carbon atom, a hydrogen atom, and a chlorine atom.

The organic halide (B) preferably has a structure (X—C—H, wherein X represents a halogen atom), in which at least one hydrogen atom and at least one halogen atom (preferably a chlorine atom) are bonded to one carbon atom. In such a structure, the C—H bond has a low dissociation energy. Thus, a radical is likely to be generated from the organic halide (B) having such a structure, and due to comparatively high stability of the radical thus generated, storage stability can be more enhanced.

The organic halide (B) preferably includes a compound represented by the following formula (2), and more preferably is the compound represented by the following formula (2).

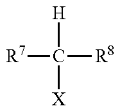

(2)

In the above formula (2): X represents a halogen atom; and $R^7$ and $R^8$ satisfy any one of following requirement A, requirement B, and requirement C.

- requirement A: $R^7$ represents a group represented by $CR^9R^{10}{=}CR^{11}$— (wherein, $R^9$, $R^{10}$, and $R^{11}$ each independently represent a hydrogen atom, a halogen atom, a monovalent hydrocarbon group, or a monovalent halogenated hydrocarbon group); and $R^8$ represents a hydrogen atom, a halogen atom, a monovalent hydrocarbon group, or a monovalent halogenated hydrocarbon group.
- requirement B: $R^7$ represents a secondary or tertiary monovalent hydrocarbon group, or a secondary or tertiary monovalent halogenated hydrocarbon group; and $R^8$ represents a hydrogen atom, a halogen atom, a monovalent hydrocarbon group, or a monovalent halogenated hydrocarbon group.
- requirement C: $R^7$ and $R^8$ each independently represent a monovalent hydrocarbon group or a monovalent halogenated hydrocarbon group.

Examples of the halogen atom which may be represented by X, $R^8$, $R^9$, $R^{10}$, or $R^{11}$ in the above formula (2) include a fluorine atom, a chlorine atom, a bromine atom, and the like, and a chlorine atom is preferred.

The monovalent hydrocarbon group which may be represented by $R^7$, $R^8$, $R^9$, $R^{10}$, or $R^{11}$ in the above formula (2) may be any one of an aliphatic hydrocarbon group and an aromatic hydrocarbon group, and an aliphatic hydrocarbon group is preferred. Examples of the aliphatic hydrocarbon group include an alkyl group, an alkenyl group, an alkynyl group, a cycloalkyl group, a cycloalkenyl group, a cycloalkynyl group, and the like, and the alkyl group or the alkenyl group is preferred and the alkyl group is more preferred. Examples of the alkyl group include a methyl group, an ethyl group, an n-propyl group, an isopropyl group, and the like. Examples of the alkenyl group include an ethenyl group, a propenyl group, and the like. The number of carbon atoms of the monovalent hydrocarbon group is preferably 1 to 6, and more preferably 1 to 4.

The monovalent halogenated hydrocarbon group which may be represented by $R^7$, $R^8$, $R^9$, $R^{10}$, or $R^{11}$ in the above formula (2) is exemplified by a group obtained by substituting at least one hydrogen atom included in the above-described monovalent hydrocarbon group, with a halogen atom (preferably, chlorine atom). The number of carbon atoms of the monovalent halogenated hydrocarbon group is preferably 1 to 6, and more preferably 1 to 4.

The secondary or tertiary monovalent hydrocarbon group which may be represented by $R^7$ in the above formula (2) is exemplified by secondary or tertiary aliphatic hydrocarbon groups such as a secondary or tertiary alkyl group and a secondary or tertiary alkenyl group, and the secondary or tertiary alkyl group is preferred. Examples of the secondary alkyl group include an isopropyl group, a sec-butyl group, and the like. Examples of the tertiary alkyl group include a tert-butyl group, a tert-pentyl group, and the like. The number of carbon atoms of the secondary or tertiary monovalent hydrocarbon group is preferably 3 to 6.

The secondary or tertiary monovalent halogenated hydrocarbon group which may be represented by $R^7$ in the above formula (2) is exemplified by a group obtained by substituting at least one hydrogen atom included in the above-described secondary or tertiary monovalent hydrocarbon group, with a halogen atom (preferably, chlorine atom). The number of carbon atoms of the secondary or tertiary monovalent halogenated hydrocarbon group is preferably 3 to 6.

$R^7$ and $R^8$ in the above formula (2) may satisfy multiple requirements among the requirement A, the requirement B, and the requirement C.

The organic halide (B) that satisfies the requirement A is a compound that generates an allyl radical upon dissociation of H (hydrogen atom) from the structure of X—C—H. Due to the allyl radical being highly stable, storage stability can be enhanced by using the organic halide (B) of such an embodiment.

In the embodiment satisfying the requirement A, $R^8$ represents preferably a hydrogen atom. $R^9$ and $R^{10}$ each represent preferably a hydrogen atom or a halogen atom, and more preferably a hydrogen atom or a chlorine atom. $R^{11}$ represents preferably a monovalent hydrocarbon group or a monovalent halogenated hydrocarbon group, more preferably an alkyl group, or a halogenated alkyl group, still more preferably a methyl group or a halogenated methyl group, and yet more preferably a methyl group or a chloromethyl group. The number of carbon atoms of $R^{11}$ is preferably 1 to 4, more preferably 1 or 2, and still more preferably 1.

Examples of the organic halide (B) that satisfies the requirement A include 1,1,3-trichloro-2-methyl-1-propene, 3-chloro-2-methyl-1-propene, 3-chloro-2-chloromethyl-1-propene, 3-chloro-1-propene, 3-chloro-1-butene, 1,1,3-trichloro-1-butene, 1,3,4-trichloro-1-butene, 1,3,3-trichloro-2-butene, and the like.

The organic halide (B) that satisfies the requirement B is a compound having a structure in which a carbon radical generated upon dissociation of H (hydrogen atom) from the structure of X—C—H is adjacent to a bulky secondary or tertiary monovalent hydrocarbon group, or a secondary or tertiary monovalent halogenated hydrocarbon group ($R^7$). This carbon radical hardly reacts with any other compound due to steric hindrance. Thus, storage stability can be enhanced even in the case of using the organic halide (B) of such an embodiment.

In the embodiment satisfying the requirement B, $R^7$ represents preferably a secondary monovalent hydrocarbon group or a secondary monovalent halogenated hydrocarbon group. Alternatively, it is also preferred that $R^7$ represents a secondary or tertiary monovalent halogenated hydrocarbon group. $R^7$ represents more preferably a secondary halogenated alkyl group or a secondary halogenated alkenyl group, and still more preferably a secondary halogenated alkyl group or a secondary chlorinated alkenyl group. The number of carbon atoms of $R^7$ is preferably 3 to 6, more preferably 3 or 4, and still more preferably 3. $R^8$ represents preferably a hydrogen atom.

Examples of the organic halide (B) that satisfies the requirement B include 1,2,3-trichloro-2-methylpropane, 1-chloro-2-methylpropane, 1-chloro-2,2-dimethylpropane, 1-chloro-2-ethylbutane, 2-ethenyl-1-chloropentane, 1,1,3-trichloro-2-methyl-1-propene, 3-chloro-2-chloromethyl-1-propene, and the like.

The organic halide (B) that satisfies the requirement C is a compound that generates a secondary radical upon dissociation of H (hydrogen atom) from the structure of X—C—H. Due to the secondary radical also being highly stable enough, storage stability can be enhanced by using the organic halide (B) of such an embodiment.

In the embodiment satisfying the requirement C, $R^7$ and $R^8$ each represent preferably an alkyl group or a halogenated alkyl group, and more preferably an alkyl group or a chlorinated alkyl group. The number of carbon atoms of $R^7$ and $R^8$ is preferably 1 to 3, and more preferably 1 or 2.

Examples of the organic halide (B) that satisfies the requirement C include 2-chlorobutane, 2-chloro-2-methylbutane, 2-chloropropane, 3-chloropentane, 3-chloro-1-pentene, and the like.

Of these, in light of a capability of exerting particularly favorable storage stability, and the like, the organic halide (B) in which $R^7$ and $R^8$ satisfy the requirement A is preferred, among compounds represented by the above formula (2). In the organic halide (B), the requirement B may be satisfied, and it is more preferred that the requirement A and the requirement B are both satisfied.

It is also preferred that the organic halide (B) includes a compound having a carbon-carbon unsaturated double bond. Such an organic halide can also exert favorable storage stability, due to superior stability of a radical to be produced, and the like. The compound having a carbon-carbon unsaturated double bond is exemplified by, among the compounds represented by the above formula (2), the compound having a carbon-carbon unsaturated double bond (in which, typically, $R^7$ and $R^8$ satisfy the requirement A), as well as 4-chloro-1-butene, 1,4-dichloro-1-butene, 4-chloro-1,3-butadiene, chloroethylene, and the like.

It is also preferred that the organic halide (B) includes a compound represented by $C_4H_5X_3$ (wherein X represents a halogen atom), and being a compound represented by $C_4H_5X_3$ is also preferred. By using such an organic halide (B), the effects of the invention that the storage stability is superior and corrosion of a metal during storage can be also inhibited are particularly favorable exerted. Examples of such an organic halide include 1,1,3-trichloro-2-methyl-1-propene, 1,1,3-trichloro-1-butene, 1,3,4-trichloro-1-butene, 1,3,3-trichloro-2-butene, and the like.

In the composition of the present invention, the content of the organic halide (B) in terms of halogen element, based on the content of the unsaturated compound (A) is 1 ppm by mass or more and 10,000 ppm by mass or less. The lower limit of the content of the halide (B) is preferably 10 ppm by mass, more preferably 30 ppm by mass, and still more preferably 50 ppm by mass, or may be yet more preferably 100 ppm by mass, 200 ppm by mass, 300 ppm by mass, 400 ppm by mass, or 500 ppm by mass. When the content of the halide (B) is equal to or more than the lower limit, storage stability of the composition can be enhanced. The upper limit of the content of the halide (B) is preferably 5,000 ppm by mass, more preferably 3,000 ppm by mass, and still more preferably 2,500 ppm by mass, or may be yet more preferably 2,200 ppm by mass, 2,000 ppm by mass, 1,600 ppm by mass, 1,300 ppm by mass, or 1,000 ppm by mass. When the content of the halide (B) is equal to or less than the upper limit, corrosion of a metal (a metal container and the like) during storage of the composition can be inhibited. Furthermore, when the content of the halide (B) is equal to or less than the upper limit, an odor of the composition can be reduced, thereby leading to an advantage that handleability can be improved.

A total content of the unsaturated compound (A) and the organic halide (B) in the composition of the present invention is preferably 95% by mass or more, more preferably 99% by mass or more, still more preferably 99.5% by mass or more, and particularly preferably 99.9% by mass or more. The total content of the unsaturated compound (A) and the organic halide (B) in the composition may be 100% by mass, or may be 99.9999% by mass or less, 99.999% by mass or less, or 99.99% by mass or less. In such a case, the composition can be particularly suitably used as a monomer material.

The organic halide (B) can be produced by a conventionally well-known method. As the organic halide (B), also a commercially available product may be used. One type, or two or more types of the organic halide (B) can be used.

Other Component(s)

The composition of the present invention may further contain an other component aside from the unsaturated compound (A) and the organic halide (B). The other component is exemplified by a solvent, an inorganic halide, water, and the like.

Examples of the inorganic halide include chlorine, hydrochloric acid, sodium chloride, and the like. In this regard, in the composition of the present invention, the content of the inorganic halide in terms of halogen element, based on the content of the unsaturated compound (A) is preferably 10 ppm by mass or less, more preferably 3 ppm by mass or less, and still more preferably 1 ppm by mass or less, or may be substantially 0 ppm by mass. In the composition of the present invention, containing no inorganic halide is preferred. When the content of the inorganic halide is thus low, corrosion of the metal can be more prevented.

Moreover, in the composition of the present invention, a content of water is preferably 10,000 ppm by mass or less, and more preferably 2,000 ppm by mass or less, 1,000 ppm by mass or less, 500 ppm by mass or less, 100 ppm by mass or less, or 50 ppm by mass or less. In the case in which the composition contains water, a hydrolysis reaction of the unsaturated compound (A) is caused to generate a carboxylic acid, whereby a part of the organic halide (B) is decomposed and thus a chlorine ion may be generated that accounts for metal corrosion. Therefore, when the content of water is equal to or less than the upper limit, corrosion of a metal can be more diminished.

Preparation Method

The preparation method of the composition of the present invention is not particularly limit, and a conventionally well-known method may be carried out. Typically, the composition can be prepared by adding a specified amount of the organic halide (B) to the unsaturated compound (A).

Intended Usage and the Like

The composition of the present invention can be used for various types of intended usages which are conventionally known as intended usages of MPDAc, etc. In particular, the composition is suitably used for synthesis of a polymer. More specifically, the composition can be used as a polymerization material in which the unsaturated compound (A) contained in the composition serves as a monomer. The composition may be a composition for polymerization. In particular, the composition can be suitably used as a material (a composition for polymerization) in producing a modified ethylene-vinyl ester copolymer (modified EVOH). In a case of using the composition for synthesis of a polymer, a favorable polymerization reaction occurs even if the organic halide (B) is decreased by a purification operation. Thus, a production method of a polymer which includes using the composition results in superior productivity.

The modified EVOH can be obtained by a production method which includes, for example, a step of copolymerizing: the unsaturated compound (A) contained in the composition of the present invention; ethylene; and a vinyl ester, and a step of saponifying a copolymer obtained. Such a modified EVOH has a characteristic feature of having enhanced stretchability and contractility, while favorable barrier properties are maintained with respect to the unmodified EVOH. Furthermore, the modified EVOH obtained by such a production method does not contain a chlorine atom in the polymer. Thus, hydrochloric acid is not generated in recycling the modified EVOH by melt kneading, leading to an advantage of easy recycling. The modified EVOH produced using a composition containing the unsaturated compound (A) and the organic halide (B) of the present invention in certain proportions has also the characteristic feature of superior recycling efficiency in melt kneading, due to a chlorine atom not being contained or a chlorine atom in a slight amount even if being contained, in the polymer.

EXAMPLES

The present invention will be described below in detail by way of Examples, but is not in any way limited to these Examples.

Compounds used in Examples and Comparative Examples are shown below.

Unsaturated compound (A)

- MPDAc: a compound represented by the following formula (A1)

Organic halide (B)

- B1: 1,1,3-trichloro-2-methyl-1-propene (a compound represented by the following formula (B1): a compound, wherein in the above formula (2), $R^7$ represents $CCl_2{=}C\ (CH_3)$—, $R^8$ represents a hydrogen atom, and X represents a chlorine atom)
- B2: 3-chloro-2-chloromethyl-1-propene (a compound represented by the following formula (B2): a compound, wherein in the above formula (2), $R^7$ represents $CH_2{=}C\ (CH_2Cl)$—, $R^8$ represents a hydrogen atom, and X represents a chlorine atom)
- B3: 1,2,3-trichloro-2-methylpropane (a compound represented by the following formula (B3): a compound, wherein in the above formula (2), $R^7$ represents $CH_2Cl$—$CCl\ (CH_3)$—, $R^8$ represents a hydrogen atom, and X represents a chlorine atom)
- B4: 2-chlorobutane (a compound represented by the following formula (B4): a compound, wherein in the above formula (2), $R^7$ represents $CH_3$—, $R^8$ represents $CH_3CH_2O$—, and X represents a chlorine atom)

(A1)

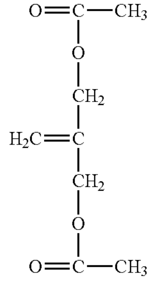

-continued (B1)

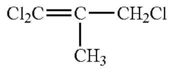

(B2)

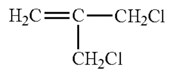

(B3)

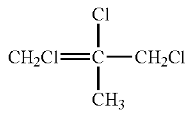

(B4)

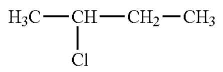

The organic halide (B1) used was produced in accordance with a production method in a publicly known document (Doctoral Dissertation Title: INVESTIGATION OF THE REACTIONS OF 1,1,3-TRICHLORO-2-METHYL-1-PROPENE AND RELATED COMPOUNDS WITH CERTAIN AROMATICS, 1955; Author: HDEI PLEDGER, JR.).

As the organic halide (B2) and the organic halide (B4), reagents commercially available from Tokyo Chemical Industry Co., Ltd. were used.

The organic halide (B3) used was produced in accordance with a publicly known document, Chemicke Zvesti; Vol. 27, No. 3, page 355 to page 358 (1973) (Title: Identification of the higher-boiling products resulting from chlorination of isobutylene).

Further, MPDAc and the organic halides (B1) to (B4) were used in each of Examples and Comparative Examples, after each moisture content was decreased to 10 ppm or less by nitrogen bubbling or by using a molecular sieve 3A.

Example 1

(1) Storage Stability Test at 40° C. After One Month

A solution of MPDAc prepared by diluting 100 times with acetonitrile was subjected to gas chromatography (analytical instrument: GC-2014 (manufactured by Shimadzu Corporation), detector: FID (hydrogen flame ionization detector), column: Rxi-5 ms (length: 30 m, film thickness: 0.25 μm, and internal diameter: 0.25 mm, manufactured by RESTEK Corporation), analytical conditions: temperature of vaporization chamber: 230° C., temperature 9f detector: 300° C., temperature rise condition: After maintaining at 50° C. for 3 min, the temperature was raised to 250° C. at a rate of 10° C./min, and then maintained at 250° C. for 10 min)), and a peak area of MPDAc detected at a retention time of 12.1 min was measured. Subsequently, 99.90 parts by mass of MPDAc and 0.10 parts by mass of the organic halide (B1) were mixed in the air at 23° C., whereby a mixed liquid (composition) of Example 1 was obtained. A content of the organic halide (B1) in terms of halogen element, based on a content of MPDAc in the mixed liquid thus obtained was 673 ppm by mass. An aliquot of this mixed liquid was removed therefrom and similarly diluted, and a thus diluted liquid was subjected to gas chromatography to measure the peak area of MPDAc. The content of MPDAc in the mixed liquid was determined from a peak area ratio (the peak area of MPDAc in the mixed liquid/the peak area of MPDAc of the liquid of MPDAc alone). The content of MPDAc in the mixed liquid before storage is shown in Table 1. Next, the mixed liquid was enclosed into a 100 mL glass bottle. It is to be noted that before enclosing, 1 mL of the mixed liquid was removed and the content of MPDAc in the mixed liquid before storage was measured. The mixed liquid enclosed into the glass bottle was stored in a thermoregulated bath at 40° C. for one month. After the storage, the temperature was equilibrated to 23° C., and the mixed liquid was diluted under a similar condition. The liquid diluted was subjected to gas chromatography, and the peak area of MPDAc was measured. The content of MPDAc after storage at 40° C. for one month was determined from a peak area ratio (the peak area of MPDAc in the mixed liquid after storage/the peak area of MPDAc in the liquid of MPDAc alone not subjected to the storage test). The content of MPDAc in the mixed liquid after storage is shown in Table 1. In addition, a percentage of the content of MPDAc in the mixed liquid after storage with respect to the content of MPDAc in the mixed liquid before storage was determined as a proportion of undecomposed MPDAc. The results are shown in Table 1. As shown in Table 1, the proportion of undecomposed MPDAc was high even after storage at 40° C. for one month.

(2) Corrosion Resistance Test of Iron Container

To 100 parts by mass of the mixed liquid of MPDAc and the organic halide produced in (1) described above were further added 0.2 parts by mass of water, and stored in an iron-pail can having a volume capacity of 20 L was reserved at 40° C. for one month. 0.5 g of the mixed liquid after reserving for one month was placed in a pressure container made of Teflon (registered trademark), and 5 mL of conc. nitric acid was added thereto and decomposition was permitted at room temperature for 30 min. Thereafter, a lid was attached and decomposition was allowed by heating with a wet decomposition system ("MWS-2", available from Actac Project Services Corporation) at 150° C. for 10 min and then at 180° C. for 5 min, followed by cooling to room temperature. This treatment liquid was transferred to a 50 mL volumetric flask (made of TPX) and diluted to fill up with pure water. This solution was subjected to an analysis of an iron element content with an ICP emission spectrometer ("OPTIMA 4300 DV", manufactured by PerkinElmer, Inc.) Based on the iron content, corrosion resistance was evaluated according to the following criteria.

A: less than 5 ppm

B: 5 ppm or more and less than 10 ppm

C: 10 ppm or more

The results are shown in Table 1. The iron content in the mixed liquid was less than 5 ppm, whereby corrosion of iron was not ascertained.

(3) Evaluation of Polymerizability (3-1) Synthesis of Modified Ethylene-Vinyl Acetate Copolymer An MPDAc mixed liquid (composition) was prepared by mixing 99.90 parts by mass of MPDAc and 0.10 parts by mass of the organic halide (B-1). Into a 250 L pressurized reactor equipped with a jacket, a stirrer, a nitrogen-feeding port, an ethylene-feeding port and an initiator-adding port, 100 kg of vinyl acetate (hereinafter, may be referred to as VAc), 10 kg of methanol (hereinafter, may be referred to as MeOH), and 2.9 kg of the MPDAc mixed liquid were charged, and then were heated to 60° C. Thereafter, nitrogen replacement in the reactor was carried out for 30 min by bubbling nitrogen. Then, ethylene was introduced into the reactor so as to give the pressure (ethylene pressure) of 4.9 MPa. After regulating the temperature in the reactor to 60° C., 60 g of 2,2'-azobis(2,4-dimethylvaleronitrile) ("V-65" available from Wako Pure Chemical Industries, Ltd.) as an initiator was added in a methanol solution to start polymerization. During the polymerization, the ethylene pressure was maintained at 4.9 MPa and the polymerization temperature was maintained at 60° C. Six hours later, when the rate of polymerization of VAc reached 45%, the polymerization was stopped by cooling. The reactor was opened to remove ethylene, and then a nitrogen gas was bubbled to completely remove ethylene. Then, after unreacted VAc was removed under a reduced pressure, MeOH was added to a modified ethylene-vinyl acetate copolymer (hereinafter, may be referred to as modified EVAc) to which a structural unit derived from MPDAc had been introduced by copolymerization to give a 20% by mass solution in MeOH.

(3-2) Saponification of Modified EVAc

Into a 500 L reactor equipped with a jacket, a stirrer, a nitrogen-feeding port, a reflux condenser and a solution-adding port, the 20% by mass modified EVAc solution in MeOH obtained in (3-1) was charged. While nitrogen gas was blown into the solution, the temperature of the solution was elevated to 60° C., and 0.5 equivalent of sodium hydroxide with respect to the vinyl acetate unit in the modified EVAc was added as a 2 N solution in MeOH. After completion of the addition of sodium hydroxide solution in MeOH, the mixture was stirred for 2 hours to allow the saponification reaction to proceed while the temperature in the system was maintained at 60° C., and methyl acetate and MeOH were distilled off. Thereafter, acetic acid was added to stop the saponification reaction. Then, ion-exchange water was added to the mixture while the mixture was stirred under heating at 60 to 80° C., whereby MeOH and water were distilled away from the reactor to permit deposition of a modified ethylene-vinyl alcohol copolymer (hereinafter, may be referred to as "modified EVOH"). Thus deposited modified EVOH was collected and was ground with a mixer. The modified EVOH powder thus obtained was charged into a 1 g/L aqueous acetic acid solution (at a liquor ratio of 20=the ratio of 20 L of the aqueous solution to 1 kg of the powder), and the mixture was stirred and washed for 2 hours. The mixture was deliquored, further charged into a 1 g/L aqueous acetic acid solution (at a liquor ratio of 20), and then stirred and washed for 2 hours. After deliquoring, an operation including: charging the matter thus deliquored to ion-exchange water (at a liquor ratio of 20); stirring and washing the mixture for 2 hours; and deliquoring the mixture was repeated three times to carry out purification. Then, after immersion with stirring in 10 L of an aqueous solution containing 0.5 g/L acetic acid and 0.1 g/L of sodium acetate for four hours, deliquoring was conducted, followed by drying for 16 hours at 60° C. to give roughly dried modified EVOH. The modified EVOH thus obtained had a melt flow rate (MFR) (at 190° C., under a load of 2,160 g) of 8.0 g/10 min.

(3-3) Content of Each Structural Unit in Modified EVAc

In the modified EVAc, the content of ethylene units, the content of structural units derived from vinyl acetate, and the content of structural units derived from MPDAc were calculated by $^1$H-NMR measurement of the modified EVAc before saponification. First, a small amount of a solution in MeOH of the modified EVAc obtained in (3-1) was sampled, and the modified EVAc was precipitated in ion exchanged water. Precipitates were collected and dried at 60° C. under vacuum to give dried modified EVAc. Next, the dried modified EVAc thus obtained was dissolved in dimethyl sulfoxide (DMSO)-d6 containing tetramethylsilane as an internal standard substance, and the measurement was carried out by using 500 MHz $^1$H-NMR (manufactured by JEOL, Ltd.: "GX-500") at 80° C.

Each peak in the $^1$H-NMR spectrum of the modified EVAc is assigned as follows:

from 0.6 to 1.0 ppm: methylene proton (4H) in a terminal region of the ethylene unit;

from 1.0 to 1.85 ppm: methylene proton (4H) in an intermediate region of the ethylene unit, methylene proton (2H) in a main chain portion of the structural unit derived from MPDAc, methylene proton (2H) of the vinyl acetate unit;

from 1.85 to 2.1 ppm: methyl proton (6H) of the structural unit derived from MPDAc and methyl proton (3H) of the vinyl acetate unit;

from 3.7 to 4.1 ppm: methylene proton (4H) in a side chain portion of the structural unit derived from MPDAc;

from 4.4 to 5.3 ppm: methine proton (1H) of the vinyl acetate unit

In accordance with the above assignment, when the integral value of from 0.6 to 1.0 ppm is denoted as x, the integral value of from 1.0 to 1.85 ppm is denoted as y, the integral value of from 3.7 to 4.1 ppm is denoted as z, and the integral value of from 4.4 to 5.3 ppm is denoted as w, the ethylene unit content (a: mol %), the vinyl ester unit content (b: mol %) and the content of the structural unit derived from MPDAc (c: mol %) are calculated in accordance with the following equations, respectively.

$$a=(2x+2y-z-4w)/(2x+2y+z+4w)\times 100$$

$$b=8w/(2x+2y+z+4w)\times 100$$

$$c=2z/(2x+2y+z+4w)\times 100$$

As a result of calculation by the above procedure, the modified EVAc had the ethylene unit content (a) of 38.0 mol %, the vinyl ester unit content (b) of 60.5 mol %, and content (c) of the structural unit derived from MPDAc being 1.5 mol %. The values of a, b, and c in the modified EVAc were the same as the values of a, b, and c in the modified EVOH after the saponification treatment.

(4) Degree of Saponification of Modified EVOH

The modified EVOH after saponification was also subjected to the $^1$H-NMR measurement in a similar manner. The roughly dried modified EVOH obtained in (3-2) was dissolved in dimethyl sulfoxide (DMSO)-d6 containing tetramethylsilane as an internal standard substance and trifluoroacetic acid (TFA) as an additive, and was subjected to the measurement at 80° C. by using a 500 MHz 1H-NMR spectrometer ("GX-500" manufactured by JEOL, Ltd.). As a result of the $^1$H-NMR measurement, since the peak intensity of from 1.85 to 2.1 ppm drastically decreased, it is clear that the ester group contained in the structural unit derived from MPDAc, in addition to the ester group derived from vinyl acetate in the modified EVOH, was also saponified to be hydroxyl group. The degree of saponification was calculated from the peak intensity ratio of the methyl proton of the vinyl acetate unit (from 1.85 to 2.1 ppm) and the methine proton of the vinyl alcohol unit (from 3.15 to 4.15 ppm). The degree of saponification of the modified EVOH of Example 1 was 99.9 mol % or more.

From the foregoing results, it was confirmed that a modified EVOH can be obtained by using the mixed liquid (composition) containing a small amount of the organic halide with respect to MPDAc.

Examples 2 to 7, Comparative Examples 1, 2

The storage stability test and the corrosion resistance test were performed similarly to Example 1, except that in each formulation of the mixed liquid (composition) of MPDAc and the organic halide, changes were carried out such that the type of the organic halide, and the mixing proportion of MPDAc and the organic halide were as shown in Table 1. In Comparative Example 1, the organic halide was not used. The results are shown in Table 1.

It is to be noted that in each mixed liquid (composition) of Examples 1 to 7 and Comparative Examples 1 and 2, any of the content of the inorganic halide in terms of halogen element, based on the content of MPDAc was 0 ppm by mass.

TABLE 1

| | Composition | | | | | Storage stability test | | | |
|---|---|---|---|---|---|---|---|---|---|
| | MPDAc | organic halide | | | inorganic halide | before storage | after storage | | |
| | mixing proportion parts by mass | type — | mixing proportion parts by mass | content in terms of halogen element ppm by mass | content in terms of halogen element ppm by mass | MPDAc content mass % | MPDAc content mass % | proportion of undecomposed MPDAc mass % | Corrosion resistance test — |
| Example 1 | 99.90 | B1 | 0.10 | 673 | 0 | 99.90 | 97.07 | 97.2 | A |
| Example 2 | 99.70 | B1 | 0.30 | 2,020 | 0 | 99.70 | 98.22 | 98.5 | A |
| Example 3 | 99.95 | B1 | 0.05 | 337 | 0 | 99.95 | 96.79 | 96.8 | A |
| Example 4 | 99.995 | B1 | 0.005 | 34 | 0 | 99.995 | 96.53 | 96.5 | A |
| Example 5 | 99.88 | B2 | 0.12 | 673 | 0 | 99.88 | 96.85 | 97.0 | A |
| Example 6 | 99.90 | B3 | 0.10 | 673 | 0 | 99.90 | 96.87 | 97.0 | A |
| Example 7 | 99.82 | B4 | 0.18 | 673 | 0 | 99.82 | 96.60 | 96.8 | A |
| Comparative Example 1 | 100.00 | — | 0.00 | 0 | 0 | 100.00 | 96.00 | 96.0 | A |
| Comparative Example 2 | 98.00 | B1 | 2.00 | 13,467 | 0 | 98.00 | 96.99 | 99.0 | C |

As shown in Table 1, in each mixed liquid (composition) of Examples 1 to 7, the proportion of undecomposed MPDAc after storage was as high as 96.5% by mass or more, suggesting superior storage stability. Furthermore, in each mixed liquid (composition) of Examples 1 to 7, corrosion of the metal during the storage was also inhibited. On the other hand, MPDAc of Comparative Example 1 not containing the organic halide was inferior in the storage stability. Moreover, in the mixed liquid of Comparative Example 2 having a too high content of the organic halide, corrosion of the metal during the storage occurred.

The invention claimed is:

1. A composition comprising: an unsaturated compound represented by following formula (1); and an organic halide, wherein a content of the organic halide in terms of halogen element, based on a content of the unsaturated compound is 1 ppm by mass or more and 10,000 ppm by mass or less,

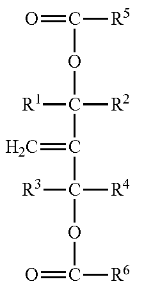

(1)

wherein, in the above formula (1), $R^1$, $R^2$, $R^3$, $R^4$, $R^5$, and $R^6$ each independently represent a hydrogen atom or an alkyl group having 1 to 10 carbon atoms.

2. The composition according to claim 1, wherein the content of the unsaturated compound is 95% by mass or more.

3. The composition according to claim 1, wherein a content of an inorganic halide in terms of halogen element, based on the content of the unsaturated compound is 10 ppm by mass or less.

4. The composition according to claim 1, wherein the organic halide comprises a compound represented by following formula (2):

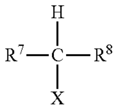

(2)

wherein, in the above formula (2): X represents a halogen atom; and $R^7$ and $R^8$ satisfy any one of following requirement A, requirement B, and requirement C, requirement A: $R^7$ represents a group represented by $CR^9R^{10}{=}CR^{11}$— (wherein, $R^9$, $R^{10}$, and $R^{11}$ each independently represent a hydrogen atom, a halogen atom, a monovalent hydrocarbon group, or a monovalent halogenated hydrocarbon group); and $R^8$ represents a hydrogen atom, a halogen atom, a monovalent hydrocarbon group, or a monovalent halogenated hydrocarbon group;

requirement B: $R^7$ represents a secondary or tertiary monovalent hydrocarbon group, or a secondary or tertiary monovalent halogenated hydrocarbon group; and $R^8$ represents a hydrogen atom, a halogen atom, a monovalent hydrocarbon group, or a monovalent halogenated hydrocarbon group;

requirement C: $R^7$ and $R^8$ each independently represent a monovalent hydrocarbon group or a monovalent halogenated hydrocarbon group.

5. The composition according to claim 4, wherein $R^7$ and $R^8$ in the above formula (2) satisfy the requirement A.

6. The composition according to claim 1, wherein the organic halide comprises a compound having a carbon-carbon unsaturated double bond.

7. The composition according to claim 1, wherein the organic halide comprises a compound represented by $C_4H_5X_3$ (wherein, X represents a halogen atom).

8. The composition according to claim 1, which is for use in synthesis of a polymer.

* * * * *